United States Patent
Goldberg et al.

(10) Patent No.: US 10,478,403 B1
(45) Date of Patent: *Nov. 19, 2019

(54) INTRAOPERATIVE TOPICALLY-APPLIED NON-IMPLANTABLE RAPID RELEASE PATCH

(71) Applicant: Privo Technologies, Inc., Peabody, MA (US)

(72) Inventors: Manijeh Nazari Goldberg, Newburyport, MA (US); Brandon LaPorte, Methuen, MA (US); Aaron Manzi, Atkinson, NH (US); Amani Jahjaa, Quincy, MA (US)

(73) Assignee: Privo Technologies, Inc., Peabody, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/970,513

(22) Filed: May 3, 2018

Related U.S. Application Data

(60) Provisional application No. 62/500,824, filed on May 3, 2017.

(51) Int. Cl.
 *A61K 9/70* (2006.01)
 *A61L 27/34* (2006.01)
 (Continued)

(52) U.S. Cl.
 CPC .......... *A61K 9/7007* (2013.01); *A61K 9/5036* (2013.01); *A61K 9/5161* (2013.01);
 (Continued)

(58) Field of Classification Search
 CPC .... A61K 9/5036; A61K 9/5161; A61K 9/006; A61K 47/36
 See application file for complete search history.

(56) References Cited

U.S. PATENT DOCUMENTS

| 4,895,724 A | 1/1990 | Cardinal et al. |
| 2003/0017195 A1 | 1/2003 | Mitragotri et al. |

(Continued)

FOREIGN PATENT DOCUMENTS

| AU | 2014218717 B2 | 8/2014 |
| WO | WO 2014/130866 A2 | 8/2014 |

OTHER PUBLICATIONS

Lee et al. (Polymer, 42: 1879-1892 (2001)).*

(Continued)

*Primary Examiner* — Kortney L. Klinkel
(74) *Attorney, Agent, or Firm* — Sunstein Kann Murphy & Timbers LLP

(57) ABSTRACT

A device for delivery of a therapeutic agent to a surgical cavity, including: a porous, mucoadhesive, freeze-dried polymeric matrix having first and second opposed surfaces, the matrix formed by a composition including chitosan; a plurality of particles embedded within the matrix, the particles containing the therapeutic agent and having a coating around the therapeutic agent, the coating including chitosan; and an additive selected from the group consisting of a hydration promoter, a particle adhesion inhibitor, a particle aggregation inhibitor, and combinations thereof. The first surface of the matrix is configured to be applied to the surgical cavity; the device releases the particles through the first surface; the device is also sterilized and provides release of approximately 20% to 100% of the therapeutic agent within 20 minutes of application to the surgical cavity.

21 Claims, 10 Drawing Sheets

(51) Int. Cl.
         A61K 31/722        (2006.01)
         A61L 26/00         (2006.01)
         A61L 15/44         (2006.01)
         A61K 47/36         (2006.01)
         A61K 9/51          (2006.01)
         A61K 9/50          (2006.01)
(52) U.S. Cl.
     CPC ............ *A61K 31/722* (2013.01); *A61K 47/36*
                      (2013.01); *A61L 15/44* (2013.01); *A61L*
                 *26/0066* (2013.01); *A61L 26/0095* (2013.01);
                                         *A61L 27/34* (2013.01)

(56)                    References Cited

U.S. PATENT DOCUMENTS

| | | | |
|---|---|---|---|
| 2004/0151774 A1* | 8/2004 | Pauletti | ................ A61K 9/0034 |
| | | | 424/486 |
| 2008/0220030 A1 | 9/2008 | Fernandez et al. | |
| 2009/0018479 A1* | 1/2009 | McCarthy | ................ A61F 13/20 |
| | | | 602/43 |
| 2011/0044911 A1 | 2/2011 | Akhtari et al. | |
| 2011/0111011 A1* | 5/2011 | Giovinazzo | .......... A61K 9/0056 |
| | | | 424/443 |
| 2011/0287110 A1 | 11/2011 | Dewhirst et al. | |
| 2012/0009260 A1 | 1/2012 | Schobel et al. | |
| 2014/0234212 A1 | 8/2014 | Goldberg et al. | |
| 2017/0329189 A1 | 11/2017 | Kim et al. | |

OTHER PUBLICATIONS

Engineering 360 ("Acrylic Adhesives and Acrylate Adhesives Information", http://www.globalspec.com/learnmore/materials_chemicals/adhesives/acrylic_methacrylate_adhesives, accessed Nov. 6, 2017).*
Kotiyan et al. (Polymers for Advanced Technologies, 13: 137-143 (2002)).*
American Cancer Society, "What Is Melanoma Skin Cancer?," 5 pages, retrieved from the internet on Apr. 6, 2017 [http://www.cancer.org/cancer/skincancer-melanoma/detailedguide/melanoma-skincancer-what-is-melanoma].
American Cancer Society, "Causes, Risk Factors, and Prevention," Colorectal Cancer detailed guide, 17 pages, retrieved from the Internet on Mar. 8, 2017 [https://www.cancer.org/cancer/colon-rectal-cancer.html].
American Cancer Society, "Understanding Advanced Cancer, Metastatic Cancer, and Bone Metastasis," American Cancer Society, 8 pages, retrieved from the internet on Jul. 23, 2018 [https://www.cancer.org/treatment/understanding-your diagnosis/advanced-cancer/what-is . . . ].
Bardot, P.M., et al., "Chitine et Chitosane Du Biopolymère à l'application" (French) Paperback; Presses universitaires de Franche-Comte', ISBN: 2-84867-249-8, 299 pages (Mar. 2009).
Barker N., et al. "The intestinal stem cell," *Genes & Dev.*, vol. 22, pp. 1856-1864 (2008).
Bhandari, B., et al. (Editors), "Nutrient Digestion and Absorption in the Gastrointestinal Tract," *Food Materials Science and Engineering*, Section 8.2, 2 pages (Aug. 2012).
Cancer Treatment Centers of America, "Hyperthermic intraperitoneal chemotherapy (HIPEC)", 2 pages, retrieved from the internet on Jul. 20, 2017.
Children's Hospital of Pittsburgh of UPMC, "Enema Administration," 2 pages, retrieved from the internet on Mar. 7, 2017 [http://www.chp.edu/our-services/surgery-pediatric/pediatric-surgery-services-we-offer/colorectal-center-for-children/patient-family-resources/enema-adminstration].
Dai T., et al., "Chitosan preparations for wounds and burns: antimicrobial and wound-healing effects," *Expert Rev. Anti. Infect. Therapy*, vol. 9, No. 7, pp. 857-879 (Jul. 2011).

Dillekås H, et al., "Differences in metastatic patterns in relation to time between primary surgery and first relapse from breast cancer suggest synchronized growth of dormant micrometastases," *Breast Cancer Res. Treat.*, vol. 146, No. 3, pp. 627-636 (2014).
Familydoctor.org, "Burning: Preventing Burns in Your Home," 3 pages, retrieved from the Internet on Apr. 6, 2017 [https://familydoctor.org/burns-preventing-burns-in-your-home/].
Fightcolorectalcancer.org, "Managing Side Effects," 7 pages, retrieved from the internet on Mar. 7, 2017 [http://fightcolorectalcancer.org/fight-it/managing-side-effects/].
Gillenwater A., et al., "Oral Premalignancy: New Methods of Detection and Treatment," *Curr. Oncol. Rep.*, vol. 8, No. 2, pp. 146-154 (Mar. 2006).
Gisbert J. P., et al., "Inflammatory Bowel Disease in the Elderly," *Ailment Pharmacol. Ther.*, vol. 39, No. 5, pp. 459-477 (2014).
Glynne-Jones, R., et al., "Anal cancer: ESMO Clinical Practice Guidelines for diagnosis, treatment and follow-up," *Annals of Oncology*, vol. 21, Suppl. 5, pp. v87-v92 (2010).
Gupta K.C., et al., "Drug release behavior of beads and microgranules of chitosan," *Biomaterials*, vol. 21, Issue 11, pp. 1115-1119 (Jun. 2000).
Hall D., "The Three Phases of the Food Digestion Process," Livestrong.com, 14 pages, retrieved from the Internet on Mar. 7, 2017 [http://www.livestrong.com/article/312184-the-three-phases-of-the-food-digestion-process/].
Harless W.W., et al., "Revisiting perioperative chemotherapy: the critical importance of targeting residual cancer prior to wound healing," *BMC Cancer*, vol. 9, No. 118, 9 pages (Apr. 2009).
Hanauer S.B., et al., "Budesonide Enema for the Treatment of Active, Distal Ulcerative Colitis and Proctitis: A Dose-Ranging Study," *Gastroenterology*, vol. 115, No. 3, pp. 525-532 (Sep. 1998).
Henderson R., "Prescribing for Children," *Patient Platform Limited*, 3 pages, retrieved from the Internet on Mar. 7, 2017 [http://patient.info/doctor/prescribing-for-children].
Hookman P., et al., "*Clostridium difficile* associated infection, diarrhea and colitis," *World Journal of Gastroenterology*, vol. 15, No. 13, pp. 1554-1580 (Apr. 2009).
Jacobson J.J., et al., "The cost burden of oral, oral pharyngeal, and salivary gland cancers in three groups: commercial insurance, medicare, and medicaid," *Head and Neck Oncology*, vol. 4, No. 15, 17 pages (2012).
Khan A., et al., "Burns: Types, Treatments, and More," Healthline Newsletter, 15 pages, retrieved from the internet on Apr. 5, 2017 [http://www.healthline.com/health/burns?m=0#Overview1].
Koh P.K., et al., "A systematic review of the function and complications of colonic pouches," *Int. J. Colorectal Dis.*, vol. 22, pp. 543-548 (2007).
Kulkarnia A.R., et al., "In-vitro release kinetics of cefadroxil-loaded sodium alginate interpenetrating network beads," *European Journal of Pharmaceutics and Biopharmaceutics*, vol. 51, No. 2, pp. 127-133 (Mar. 2001).
Lai S.K., et al., "Mucus-penetrating nanoparticles for drug and gene delivery to mucosal tissues," *Adv. Drug Deliv. Rev.*, vol. 61, No. 2, pp. 158-171 (Feb. 2009).
Laksitorini M., et al., "Pathways and Progress in Improving Drug Delivery Through the Intestinal Mucosa and Blood-Brain Barriers," *Ther. Deliv.*,vol. 5, No. 10, pp. 1143-1163 (Oct. 2014).
Liu Z., et al., "Polysaccharides-based nanoparticles as drug delivery systems," *Adv. Drug Deliv. Rev.*, vol. 60, No. 15, pp. 1650-1662 (Dec. 2008).
Macrae F.A., et al., "Clinical presentation, diagnosis, and staging of colorectal cancer," *UpToDate*, 20 pages, retrieved from the Internet on Mar. 8, 2017 [http://www.uptodate.com/contents/clinical-presentation-diagnosis-and-staging-of-colorectal-cancer].
Makarios-Laham I., et al., "Biodegradability of Chitin- and Chitosan-Containing Films in Soil Environment," *Journal of Environmental Polymer Degradation*, vol. 3, No. 1, pp. 31-16 (Jan. 1995).
MDconsult.com, "Anatomy and Histology of the Small and Large Intestine," 18 pages, retrieved from the Internet on Mar. 8, 2017 [http://jpck.zju.edu.cn/jcyxjp/files/ge/05/MT/0511.pdf].
Misono S., et al., "Incidence of Suicide in Persons With Cancer," *Journal of Clinical Oncology*, vol. 26, No. 29, pp. 4731-4738 (Oct. 10, 2008).

(56) References Cited

OTHER PUBLICATIONS

Mulcahy M., "When Fighting Cancer Isn't Worth It," *The Atlantic—Health*, 5 pages (Dec. 2012).
Murata Y., et al., "Use of floating alginate gel beads for stomach-specific drug delivery," *Eur. J. Pharm. Biopharm.*, vol. 50, Issue 2, pp. 221-226 (Sep. 2000).
Nagpal K., et al., "Chitosan Nanoparticles: A Promising System in Novel Drug Delivery," *Chemical and Pharmaceutical Bulletin*, vol. 58, No. 11, pp. 1423-1430 (Nov. 2010).
National Cancer Institute, "Surveillance, Epidemiology, and End Result Program (SEER),"—Cancer of the Colon and Rectum—Cancer Stat Facts, 9 pages, retrieved from the internet on Mar. 7, 2017 [https://seer.cancer.gov/statfacts/html/anus.html].
National Cancer Institute, "Surveillance, Epidemiology, and End Result program (SEER)," Cancer of the Anus, Anal Canal, and Anorectum—Cancer Stat Facts, 9 pages, retrieved from the internet on Mar. 15, 2017 [https://seer.cancer.gov/statfacts/html/colorect.html].
National Cancer Institute, "Metastatic Cancer, What Is Metastatic Cancer?," 5 pages, retrieved from internet on Jul. 20, 2018.
National Psoriasis Foundation, "50 Years Driving Discovery, Creating Community," National Psoriasis Foundation, 4 pages, retrieved from the internet on Apr. 6, 2017 [https://www.psoriasis.org/].
National Psoriasis Foundation, "Causes and Triggers," 6 pages, retrieved from the internet on Apr. 6, 2017 [https://www.psoriasis.org/about-psoriasis/causes].
New Radiant Technology S.p.A., "Novac 7, The first mobile electron linear accelerator for IORT", 6 pages, retrieved from the internet on Jul. 20, 2018 [http://sennewald.de/wp-content/uploads/novac7.pdf].
Patil P., et al., "A Review on Ionotropic Gelation Method: Novel Approach for Controlled Gastroretentive Gelispheres," *Int. J. Pharm. Pharm. Sci.* vol. 4, Suppl. 4, pp. 27-32 (2012).
Paun B.C., et al., "Postoperative Complications Following Surgery for Rectal Cancer," *Annals of Surgery*, vol. 251, No. 5, pp. 807-818 (2010).
Ryan D.P., et al., "Clinical features, staging, and treatment of anal cancer," 10 pages, retrieved from the internet on Mar. 8, 2017 [http://www.uptodate.com/contents/clinical-features-staging-and-treatment-of-anal-cancer].
Saramento B., et al., "Chitosan-Based Systems for Biopharmaceuticals: Delivery, Targeting and Polymer Therapeutics," *John Wiley & Son, Ltd.*, 564 pages (Mar. 2012).
Shaw D., et al. "Intestinal mucosal atrophy and adaptation," *World Journal of Gastroenterology*, vol. 18, Issue 44, pp. 6357-6375 (Nov. 2012).
Sperk, et al., "A cohort analysis to identify eligible patients for intraoperative radiotherapy (IORT) of early breast cancer" *Radiation Oncology*, vol. 9, No. 154, 7 pages (2014).
The HPV and Anal Cancer Foundation, "Living with Anal Cancer/ Causes & Risk Factors," 8 pages, retrieved from the internet on Mar. 7, 2017 [http://www.analcancerfoundation.org/living-with- anal-cancer/anal-cancer-risk-factors-causes/].
The HPV and Anal Cancer Foundation, "Living With Anal Cancer/ Treatment for Anal Cancer," 18 pages, retrieved from the internet on Mar. 8, 2017 [http://www.analcancerfoundation.org/living-with- anal-cancer/anal-cancer-treatment/].
The Oral Cancer Foundation, website, 3 pages, retrieved from the internet on Mar. 9, 2017 [http://oralcancerfoundation.org/].
The Oral Cancer Foundation, "Mucositis," 14 pages, retrieved from the internet on Mar. 9, 2017 [http://oralcancerfoundation.org/complications/mucositis].
Tufts Medical Center, "Cytoreductive Surgery with Hyperthermic Intraperitoneal Chemotherapy (HIPEC)," HIPEC FAQ's, 2 pages, retrieved from the internet on Jul. 20, 2018.
Tufts Medical Center, "Cytoreductive Surgery with Hyperthermic Intraperitoneal Chemotherapy (HIPEC)" 7 pages, retrieved from the internet on Jul. 20, 2018.
Tulunay O., et al., "Pilot Study of Intraoperative Chemotherapy with Cisplatin and 5-Fluorouracil in Patients with Advanced Squamous Cell Carcinoma of the Head and Neck," *Head & Neck*, vol. 29, Issue 3, pp. 267-271 (Mar. 2007).
Weinberg M.A., et al., "Assessing Oral Malignancies," *American Family Physician*, vol. 65, No. 7, pp. 1379-1384 (Apr. 2002).
West Virginia University, "Intraoperative Radiation Therapy," WVU Medicine Health Report, 3 pages, retrieved from the internet on Jul. 20, 2018 [https://www.cancercenter.com/treatments/intraoperative-radiation-therapy/].
Willett, C.G., et al., "Adjuvant therapy for resected rectal adenocarcinoma," 5 pages, retrieved from the Internet on Mar. 8, 2017 [http://www.uptodate.com/contents/adjuvant-therapy-for-resected-rectal-adenocarcinoma].
Youssef N.N., et al., "Management of Intractable Constipation With Antegrade Enemas in Neurologically Intact Children," *Journal of Pediatric Gastroenterology & Nutrition*, vol. 34, No. 4, pp. 402-405 (Apr. 2002).
Zhang H., et al., "Monodisperse Chitosan Nanoparticles for Mucosal Drug Delivery," *Biomacromolecules*, vol. 5, No. 6, pp. 2461-2468 (2004).
Zhang Z, et al., "Polymeric nanoparticles-based topical delivery systems for the treatment of dermatological diseases," *Nanomedicine and Nanobiotechnology*, vol. 5, Issue 3, pp. 205-218 (May/Jun. 2013).
Zhang Z., et al., "Effect of chitosan and carboxymethyl chitosan on fibrinogen structure and blood coagulation." *J. Biomater. Sci. Polym. Ed.*, vol. 24, No. 13, pp. 1549-1563 (2013).
M. Vázques, Lantes, Authorized officer, International Search Report—Application No. PCT/US2014/017790, 4 pages (dated May 19, 2014).
International Search Report—Application No. PCT/US2018/000065, 6 pages (dated May 28, 2018).
M. Vázquez, Lantes, Authorized Officer, Written Opinion of the International Searching Authority—Application No. PCT/US2017/018514, 7 pages (dated Aug. 24, 2017).
Bruce D. Sunstein, Esq. Sunstein Kann Murphy & Timbers LLP, Supplement to Response C—U.S. Appl. No. 15/436,651, 12 pages (filed Jun. 22, 2018).
Non-Final Office Action—U.S. Appl. No. 15/436,651, 40 pages (dated Nov. 15, 2017).
Bruce D. Sunstein, Esq. Sunstein Kann Murphy & Timbers LLP, Response B and Declaration of Manijeh Goldberg, Ph.D.—U.S. Appl. No. 15/436,651, 151 pages (filed Jan. 23, 2018).
Final Office Action—U.S. Appl. No. 15/436,651, 26 pages (dated Apr. 30, 2018).
Bruce D. Sunstein, Esq. Sunstein Kann Murphy & Timbers LLP, Response C and Request for Consideration Under the After Final Consideration Pilot Program 2.0,—U.S. Appl. No. 15/436,651, 26 pages (filed May 21, 2018).
Patrea L. Pabst Pabst Patent Group LLC, Amendment and Response to Final Office Action—U.S. Appl. No. 14/186,977, 11 pages (dated Sep. 23, 2016).
Non-Final Office Action—U.S. Appl. No. 14/186,977, 11 pages (dated Jun. 22, 2016).
U.S. Appl. No. 15/436,651, filed Feb. 17, 2017.
U.S. Appl. No. 15/897,729, filed Feb. 15, 2018.
U.S. Appl. No. 15/932,315, filed Feb. 16, 2018.

* cited by examiner

FIGURE 5A
FIGURE 5B
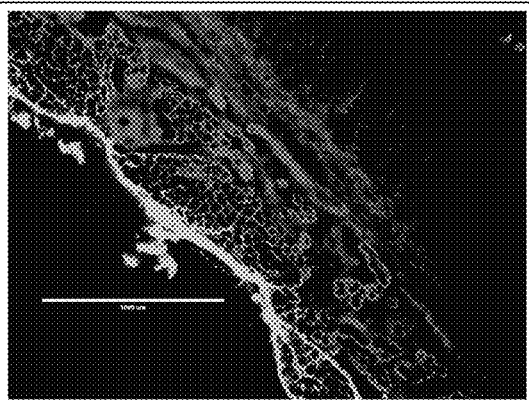
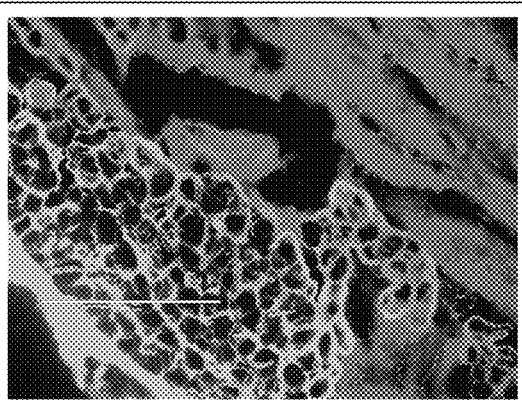
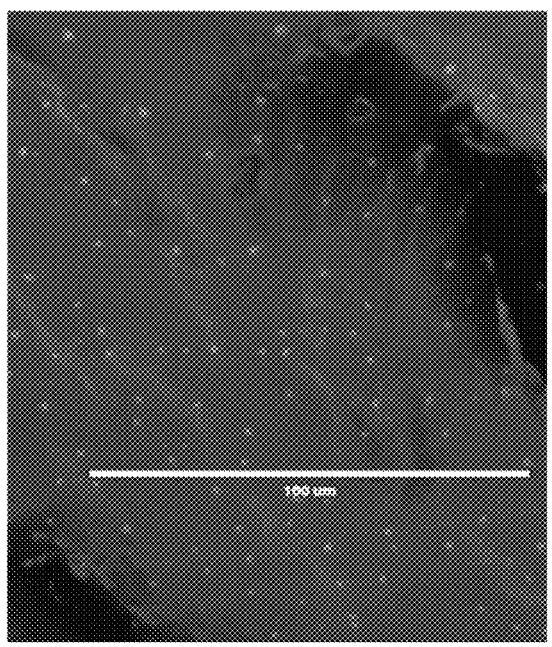
FIGURE 5C

INTRAOPERATIVE TOPICALLY-APPLIED NON-IMPLANTABLE RAPID RELEASE PATCH

CROSS REFERENCE TO RELATED APPLICATIONS

The present application claims the benefit of U.S. provisional application No. 62/500,824, filed on May 3, 2017, which is hereby incorporated herein by reference in its entirety.

TECHNICAL FIELD

The present invention is in the field of formulations for targeted rapid delivery of agents intraoperatively to surgical cavities of organs and tissue.

BACKGROUND

Survival rates and quality of life of cancer patients can be significantly improved if recurrence and further metastasis can be reduced or eliminated. When tumors are discovered, surgery is often used to resect and eliminate primary and secondary tumors. When surgery is utilized, however, the risk of metastasis and recurrent can actually increase and remains high, because the surgical cavity and surgical procedure results in an environment which promotes the spread of remaining cancer cells. For example, by cutting into human tissue, natural tissue formations and barriers are disrupted and the bloodstream can become exposed, while simultaneously, healthy and cancerous cells break apart or otherwise become freed during surgery. In many cases, this combination results in cancerous cells becoming freed and exposed to the bloodstream, and promotes eventual metastasis to additional regions, or recurrence locally/regionally.

Cancer cells are able to 'break away" from their original tumor site and travel through the bloodstream or lymphatic system to new locations, where additional cancers will start to proliferate [1, 2]. Most cancer cells that break free from the original tumor are carried in the blood or lymph until they get trapped in the next "downstream" organ or set of lymph nodes. This explains why breast cancer often spreads to underarm lymph nodes, but rarely to lymph nodes in the groin [1]. The liver is a common site of spread for cancer cells that start in the colon because blood from the intestines flows into the liver [1].

When a tumor remains intact, cancer cells sometimes metastasize to additional locations through the series of the following steps: (1) invading nearby local tissue, (2) moving through the walls of nearby lymph nodes or blood vessels, (3) traveling through the lymphatic system and/or bloodstream to other parts of the body, (4) stopping in small blood vessels at a distant location, invading the blood vessels, and moving into surrounding tissue, (5) growing in the tissue, forming large tumors [2]. Presently, few treatment options are available in response to metastatic tumors. These include additional surgery, systemic chemotherapy and radiation. However, any treatment for tumor recurrence post the second surgery will be for palliative purposes. On rare occasions, intraoperative radiation therapy (IORT) and intraoperative heated intraperitoneal chemotherapy (HIPEC) are used to deliver highly focused and intense therapy to reduce the chance of metastasis. While increase in efficacy has been shown, these intraoperative treatments remain very uncommon due to significant cost burden, large size and complexity in operation. There are also considerable risks and drawbacks associated with their use, as well as lack of widespread availability. In addition, these treatment options are limited in their targeting of tumor tissue, which hinders their efficacy and can lead to recurrence and further metastasis. This is due to the micro-metastatic risk associated with surgery.

As mentioned above, cancer cells can often "break away" from the primary tumor site and travel through the bloodstream to additional regions, forming new tumors. This risk is drastically amplified by the use of surgery, which slices into tissue and disrupts tumor and healthy tissue. Many cells are broken up and freed during surgery including cancer cells, and are simultaneously exposed to the bloodstream, which can facilitate the spread of malignant tumor cells through the bloodstream to additional sites [3].

Currently, post-surgery radiation and chemotherapy (approximately 30 days post-surgery for wound healing) is utilized; however, tumor recurrence and death still remain a major problem. The need to destroy the potential micro-metastatic cells even prior to wound healing steps post-surgery is a novel approach that can reduce the tumor recurrence post-surgery [8].

It has been shown that there are important parallels between wound healing and metastasis, and cancer cells may rely on these pathways to survive and metastasize. Primary tumor removal activates wound healing pathways as a result of the surgical trauma, the removal of the primary tumor, and the seeding of cancer cells into the circulation. These pathways are activated immediately after surgery, with the peak increase in the proliferation of residual cancer cells occurring within 24-72 hours after primary tumor removal. Allowing wound healing to occur before initiating therapy may be facilitating metastatic spread of the cancer and compromising the subsequent effectiveness of that therapy.

Intra-operative radiation therapy (IORT) and systemic intravenous chemotherapy are treatment options which can be utilized to reduce or eliminate metastatic cancer. They are utilized after a tumor is removed to eliminate remaining tumor cells. These aforementioned treatment options, however, are limited in their ability to target tumor cells, carry substantial risks and side effects, and are in many cases highly expensive and not available to significant numbers of patients. IORT is a treatment option which directs a high concentration of radiation to a surgical cavity following the resection of a cancerous tumor. IORT is commonly used in breast cancer patients, for example, following surgical tumor resection [9, 10]. A metal disk is placed behind the targeted breast tissue to spare the underlying tissue, and high concentrations of radiation are directed to the surgical cavity [10]. IORT has also shown promising results when combined with pre-operative external beam irradiation plus chemotherapy and tumor resection for high-risk patients with locally advanced primary or locally recurrent colorectal cancer. IORT is not commonly used to treat metastatic colorectal cancer.

Despite some advantages of IORT, there are significant drawbacks to the therapy, the first of which relates to the cost and commercial availability of the treatment option. The NOVAC 7 (Sordina IORT Tech, Italy) is an example machine used to administer IORT. The machine is expensive, requires skilled personnel to operate and maintain, and is not readily available. It is a large complex machine that weighs approximately 790 kg [11]. In addition, IORT is a standard procedure which is not suitable for every patient. Surprisingly, only 25% of patients are deemed to be an appropriate fit for IORT [6]. IORT adds approximately 30 minutes onto the treatment procedure, and additional radiation following tumor resection and IORT can be necessary [10].

Heated intraperitoneal chemotherapy (HIPEC) is another procedure which is commonly used to reduce or eliminate tumors from organs and surfaces within the abdomen. Like IORT, cytoreductive surgery is performed prior to HIPEC treatment [12]. HIPEC is used within the abdomen and pelvis. HIPEC is utilized for metastatic cancers on tissues including the stomach, small intestine, colon, liver, spleen, pancreas, uterus, rectum, omentum, ovaries and other peritoneal surfaces [12]. The process involves cytoreduction followed by the placement of tubes and temperature probes into the abdominal cavity [12, 13]. The skin is sutured closed, and the reverse sides of the tubes are attached to a machine which regulates temperature and flow rate. The tubes introduce a saline solution within the abdominal cavity, followed by draining and flooding of the abdominal cavity with a heated chemotherapy solution [12, 13]. The solution is heated to approximately 42-43 degrees Celsius. The abdomen is shaken to allow homogenous distribution of the solution, and the solution is subsequently drained. The abdomen is again washed with saline solution. The abdomen is then re-opened, the tubes are removed, and the abdomen is stapled closed. The entire procedure including surgery can take 6-14 hours, and the HIPEC can take in excess of 90 minutes to administer [12, 13]. Patients remain in the hospital for 10-12 days following the procedure.

The described HIPEC treatment option, while increasing in use, carries significant drawbacks, including debilitating side effects, lengthy treatment time, and poor targeting. Similarly to IORT, the machine used to administer and regulate the HIPEC solutions is expensive, requires highly specialized personnel, and is, as a consequence, not commercially available to all patients. In 2013, only 27 states in the US had at least one expert able to administer HIPEC and, as a result, those seeking HIPEC treatment are typically "highly motivated, younger, healthier and wealthier" individuals [14]. In addition, side effects can be severe, including bleeding, infection, and even death during or shortly following treatment [14]. Blood clots can also form in the legs of patients and travel to parts of the body such as the lungs. The development of an enterocutaneous fistula (opening between the intestines and abdominal skin) or anastomotic leak (a leak that may occur when sections of the intestines are surgically reconnected) can also occur [14]. In addition, fatigue can plague patients for 2-3 months following the procedure, and nutritional intake can be reduced, however this side effect is in part caused by the surgical procedures as well. Overall, 1% of people die as a result of the treatment and 12% experience serious post-operative problems [14]. In addition, the chemotherapy agent administered in solution form is "poorly absorbed by the underlying tissue" [4] and is only somewhat targeted to the large intraperitoneal cavity.

There is a desperate need for a safe intraoperative chemotherapy to minimize the risk of tumor cell implantation and metastasis during cancer surgeries such as head and neck cancers [8]. The treatment needs to be inexpensive and simple to administer to enable its widespread availability and adoption.

SUMMARY OF THE EMBODIMENTS

In one set of representative embodiments, there is provided a device for delivery of a therapeutic agent to a surgical cavity, the device comprising: a porous, mucoadhesive, freeze-dried polymeric matrix having first and second opposed surfaces, the matrix formed by a composition comprising chitosan; a plurality of particles embedded within the matrix so as to be directly surrounded by, and in contact with, the matrix, the particles containing the therapeutic agent and having a coating around the therapeutic agent, the coating comprising chitosan so as to provide controlled release of the therapeutic agent from the particles through the first opposed surface of the matrix; and an additive selected from the group consisting of a hydration promoter, a particle adhesion inhibitor, a particle aggregation inhibitor, and combinations thereof. The first surface of the matrix is configured to be applied to the surgical cavity; the device is configured to provide release of the particles through the first surface; the device is also sterilized and provides release of approximately 20% to 100% of the therapeutic agent within 20 minutes of application to the surgical cavity.

The hydration promoter may be selected from the group consisting of ethylene glycol, propylene glycol, beta-propylene glycol, glycerol, and combinations thereof. The particle adhesion inhibitor may be a non-ionic polymer, for example hydroxypropyl methylcellulose. The particle aggregation inhibitor may be selected from the group consisting of monosaccharides, disaccharides, sugar alcohols, chlorinated monosaccharides, chlorinated disaccharides, and combinations thereof. The particles may further include sodium tripolyphosphate. The device may also include a free quantity of the therapeutic agent, embedded directly in the matrix, and not otherwise coated with chitosan, wherein the free quantity of the therapeutic agent constitutes between 20-80% of a total quantity of therapeutic agent in the device. The device may further comprise a backing layer disposed on the second surface, wherein the backing layer prevents significant loss of payload components in the device from diffusion through the second surface, and optionally protects the device from an environment. The backing layer may include a material selected from the group consisting of a polyacrylate adhesive, a non-woven polyester fabric backing, or combinations thereof. The average diameter of the particles may be from about 60 nm to about 2000 nm. In some embodiments, the therapeutic agent may be a chemotherapeutic pharmaceutical, for example one selected from the group consisting of platinum-based chemotherapeutics, 5-flurouracil, and combinations thereof. The therapeutic agent may also be an agent selected from the group consisting of anti-infective, anti-bacterial, or anti-viral agent, and combinations thereof.

Also provided is a kit including the device and a permeation enhancing agent. Example permeation enhancing agents are selected from the group consisting of dodecyl-2 (N,N-dimethylamino) propionate, bile salts, surfactants, fatty acids, glycerides, polyacrylic acid derivatives, chelating agents, nitric oxide donors, salicylates, chitosan, zona occludens toxins, sodium cholate, sodium deoxycholate, sodium glycodeoxycholate, sodium taurocholate, sodium glycocholate, N-lauryl-b-maltopyranoside, and combinations thereof. Example surfactants include oleic acid, sodium dodecyl sulfate, sodium lauryl sulfate, Polysorbate 80, lauryl esters, and combinations thereof.

In a second set of representative embodiments, there is provided a method for manufacturing a rapid release delivery device for delivering a therapeutic agent to a tissue, the method comprising: forming a first mixture with a plurality of particles, the particles containing a therapeutic agent and having a coating around the therapeutic agent, the coating including chitosan; adding chitosan, a hydration promoter, a particle adhesion inhibitor, a particle aggregation inhibitor or combinations thereof to the first mixture, to form a second mixture; freezing the second mixture in a bath containing an aqueous alcoholic solution at a temperature above the freezing temperature of the aqueous alcoholic solution and at most −40° C., to form a frozen layer precursor; drying the frozen layer precursor, to form a porous patch with particles embedded within a polymeric matrix of the patch; and sterilizing the patch.

The bath may further contain dry ice. The alcohol of the aqueous alcoholic solution may be ethanol. The aqueous alcoholic solution may be from about 90 wt % ethanol to about 99 wt % ethanol. A free quantity of the therapeutic agent may be embedded directly in the matrix, and not otherwise coated with chitosan, wherein the free quantity of the therapeutic agent constitutes between 20-80% of a total quantity of therapeutic agent in the device. The patch may include first and second opposed surfaces and the first surface may be configured to be applied to the tissue, the method further comprising adhering a backing layer to the second surface of the patch, wherein the backing layer prevents significant loss of payload components in the patch from diffusion through the second surface, and optionally protects the patch from an environment. The drying may be under vacuum. The sterilizing may include gamma ray irradiation.

BRIEF DESCRIPTION OF THE DRAWINGS

The foregoing features of embodiments will be more readily understood by reference to the following detailed description, taken with reference to the accompanying drawings, in which:

FIGS. 5A, 5B, and 5C are photomicrographs showing the results from an ex vivo experiment conducted on porcine stomach tissue.

FIG. 9A is a graph showing a high-performance liquid chromatography (HPLC) chromatogram of a cisplatin standard. FIG. 9B is a graph showing an HPLC chromatogram of a patch, which illustrates that the cisplatin was not modified. FIG. 9C is a graph showing an HPLC chromatogram of a patch which underwent gamma sterilization, and further shows that cisplatin was not modified.

DETAILED DESCRIPTION OF SPECIFIC EMBODIMENTS

Figures 1A, 1B, 1C:
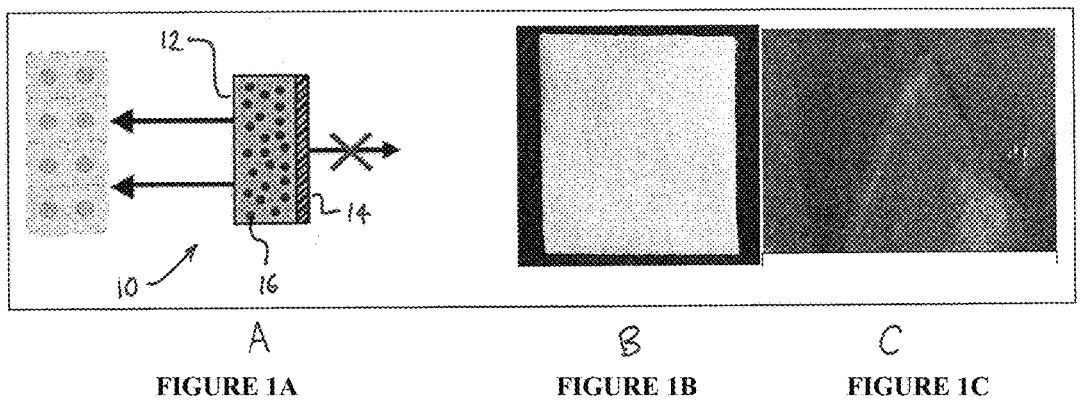
FIG. 1A is a schematic illustration of an example patch containing particles within a layer and a backing layer impermeable to significant passage of particles or agent. The patch is to be applied to tissue according to embodiments of the present invention.
FIG. 1B is a photograph showing a top view of an example patch according to embodiments of the present invention.
FIG. 1C is a photograph showing a perspective view of an example patch within a tumor cavity according to embodiments of the present invention.
Figure 2:
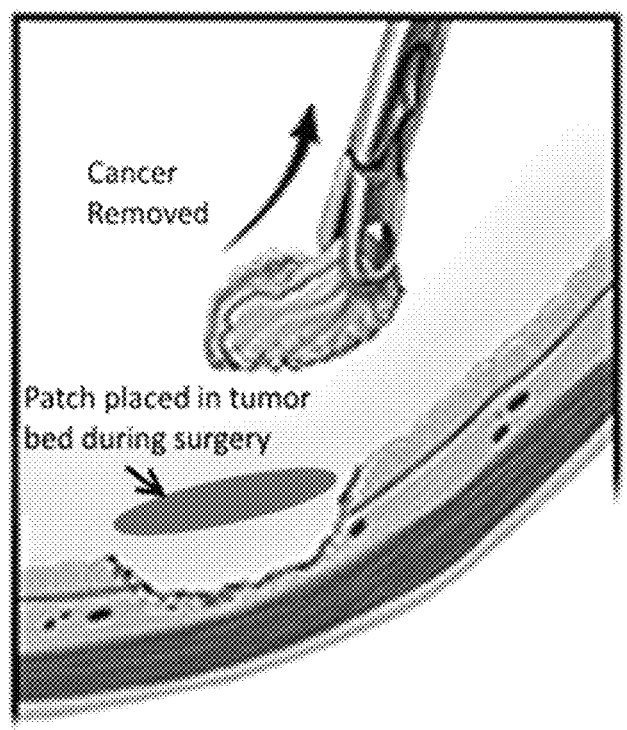
FIG. 2 schematically illustrates the placement of a patch within a tumor cavity immediately following tumor resection according to embodiments of the present invention.

Definitions. As used in this description and the accompanying claims, the following terms shall have the meanings indicated, unless the context otherwise requires:

"Patch" refers to a device, mesh, wafer, matrix, sponge or similar like product which contains elements incorporated therein to be released therefrom.

"Permeation" is the ability to pass through or penetrate underlying tissue upon which a patch has been topically applied.

"Biocompatible" refers to the ability of a biomaterial to perform its desired function with respect to a medical therapy, without eliciting any significant undesirable local or systemic effects in the recipient or beneficiary of that therapy, but generating the most appropriate beneficial cellular or tissue response in that specific situation, and optimizing the clinically relevant performance of that therapy.

"Biodegradable" refers to a property of a material rendering it capable of being broken down especially into innocuous products by the action of living organisms.

"Particles" refer to small objects having an average diameter of at least 60 nm to at most 2000 nm.

"Adhesion inhibitor" refers to an additive that lowers the attractive forces between a patch and particles embedded therein. As a result, the particles can move through the patch at a faster rate than in the absence of the adhesion inhibitor.

"Aggregation inhibitor" refers to an additive that lowers the tendency of particles embedded in a patch to aggregate when the solution which forms the patch is subjected to freeze drying. As a result, the particles are less likely to suffer from damage or destruction when the freezing takes place.

"Payload" refers to the therapeutic agents and other materials within a patch that are released from the patch upon application to tissue. The payload may include, for example, one or more components selected from the group consisting of particles, agents encapsulated within particles, freeform agents, adhesion inhibitors, aggregation inhibitors, hydration promoters, permeation enhancers, and combinations thereof.

"Polydispersity index" (PDI) or simply, "dispersity" is used herein to refer to a measure of the heterogeneity of sizes of particles in a mixture. PDI measures the size dispersity of nanoparticles.

"Zeta potential" (ZP) is used herein to refer to the overall charge that nanoparticles acquire in a particular medium and can be measured on a Zetasizer Nano instrument.

A "particle diameter" is the length of the longest axis between two points on the surface of the particle.

"HPMC" refers to hydroxypropyl methylcellulose, also known as hypromellose.

"Tissue" in the context of embodiments of the present invention refers to organ, epithelial, mucosal, or other tissue which exists within regions such as the abdomen, pelvis, intraperitoneal cavity, and/or other intraperitoneal surfaces.

"Surgical cavity" refers to the cavity, opening, site or tissue surface that results from the surgical resection of tissue.

"Rapid", "rapid release", or "rapid delivery" in reference to release from the patch refers to the release of between 20% and 100% of the patch's payload within approximately 20 minutes.

"Kilo counts per second" or "Kcps", mean count rate (in thousands of counts per second). For example, the threshold may be set such that when the count rate of the sample is lower than 100, the measurement should be aborted, meaning the concentration of the sample is too low for measurements. A sample with suitable Kcps can be considered a stable sample with an acceptable concentration for measurement.

Unless otherwise specified, the term "wt %" refers to the amount of a component of a system for delivery of a therapeutic agent, as expressed in percentage by weight.

Unless otherwise specified, the "molar mass" of a polymer is intended to mean the number average molar mass of the polymer molecules.

"Impermeable" refers to a layer not allowing a given substance to pass through. For example, a layer may be impermeable to one or more chemical compounds, and/or to particles having a diameter equal to or larger than a certain threshold value. The term "substantially impermeable" applies to instances where the layer allows the passage of minimal amounts of the substance, for example less than 1% or 2% of the total amount of the substance.

Intraoperative Rapid Release Patch

Embodiments of the present invention provide a device in the form of a patch which is topically applied following surgery to target and eliminate remaining tumor cells within the surgical cavity. As illustrated in FIGS. 1A-1C and 2, the device is able to overcome the limitations of IORT, HIPEC, systemic chemotherapy and standalone surgery due to its ability to deliver and retain a high concentration of a chemotherapeutic agent locally. The patch is placed in the bed (cavity) which is formed following resection of the tumor. The patch is able to restrict exposure of the tumor cavity to the systemic bloodstream due to chitosan's coagulant effect and rapidly release particles into the tissue which permeate and target remaining cancer cells. The device may be applied as a simple topical administration, high in safety due to the use of a small amount of highly targeted agent. The device may have an application time as low as a few minutes, which does not increase the duration of surgery since it can easily be applied while other tasks in the operating room are being performed to prepare for closing the resected region. The device can be easily manufactured and distributed for widespread commercial availability. In addition, embodiments of the present invention are able to provide higher efficacy than other treatment options due to local targeting and retention.

Figure 3:
FIG. 3 is an image of an abdominal cavity with a patch topically placed upon affected tissue within the abdominal cavity to treat cancerous cells according to embodiments of the present invention.

Also as illustrated in FIGS. 1A-1C and as further illustrated in FIG. 3, the patch provides rapid delivery of one or more agents to the surgical cavity, preventing the spread of cancerous cells, and offering a high degree of agent retention to the applied tissue and to tumor cells. The patch is applied and topically adheres to the desired organ or tissue, for example the bed of the tumor surface within stomach, small intestine, colon, pancreas, spleen, liver, rectum, uterus, ovaries, and peritoneal surface tissue, as exemplified in FIG. 3. The topical placement of the patch allows delivery of the patch's payload to the underlying cells. The particles in the payload penetrate the tissue and release the agent or agents directly into the tissue. Multiple patches may also be used to treat cancer affecting a number of locations.

Figure 4:
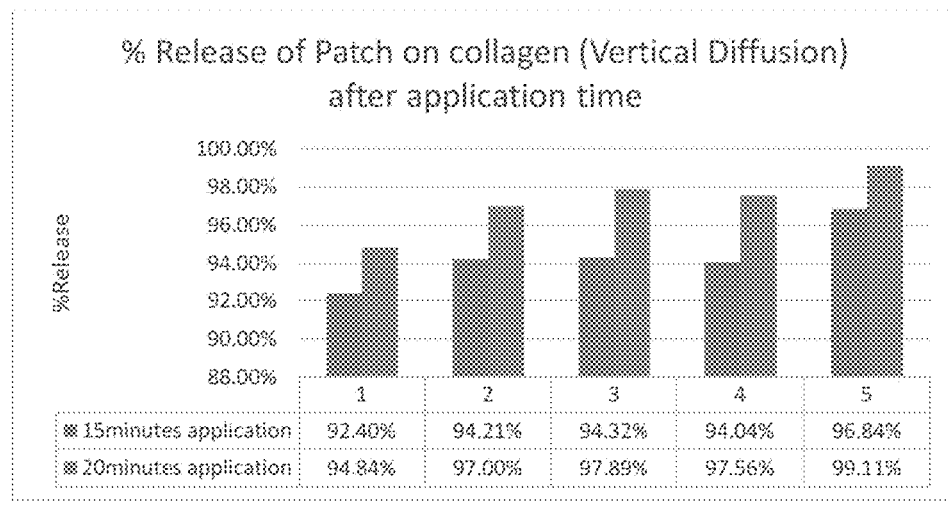
FIG. 4 is a bar graph showing the results of a vertical diffusion experiment which was conducted to observe the release profile of one embodiment of the present invention.

The novelty of this patch lies in part with its property of rapid therapeutic agent release. Unlike other implantable patches which provide slow sustained agent release, the patch of the present application has been primarily designed to allow for rapid agent release. The percentage of agent released in a rapid fashion can be modulated depending on a desired preference, and the release from the patch is able to range from a minimum of 20% release to a maximum of 100% release within approximately 20 minutes or less. As such, the payload of the patch is released up to approximately 20 minutes following surgery, after which the patch is removed and disposed of. FIG. 4 is a bar graph showing the results of a vertical diffusion experiment which was conducted to observe the release profile of example patches according to one embodiment of the present invention. Five samples were tested for this particular experiment. Vertical diffusion was conducted on a collagen membrane to gauge the release profile of one embodiment of the present invention. This embodiment included the agent cisplatin encapsulated within chitosan particles with a range in size of approximately 500 nm. The particles were released onto the collagen, after which they were allowed to diffuse into the underlying solution. As shown, between 92.40% and 96.84% of the particles and agent within the patch were released after 15 minutes, and between 94.84% and 99.11% of the particles and agent were released from the patch after 20 minutes. This is one of a number of experiments which have confirmed the rapid release properties of example patches according to embodiments of the present invention.

While implantable wafers are being developed that are intended for slow release of agents over several months, the patch of the present application is rather intended for non-implantable, intraoperative use where rapid release of all embedded agent is required during the surgery and its retention in the tumor bed is essential for its successful application. In addition to uses in complete tumor resection surgery, the patch may be used for other intraoperative applications, for example in the context of procedures known as cytoreductive surgery or debulking where, due to complications, the tumor cannot completely be removed. As such, the surgery is frequently used only as a means of reducing tumor size, leaving some tumor tissue behind. In these instances, the patch can be easily applied to the remaining tumor since it can be fitted in hard to reach and operate regions by virtue of its pliability, its small size and its flexibility. The patch then can be removed when the wound is ready for closure.

As illustrated in FIG. 1A, a patch 10 includes a layer 12 having first and second opposed surfaces and a backing layer 14 adjacent to one of the surfaces. Layer 12 contains at least one therapeutic agent and a porous, mucoadhesive polymeric matrix that is formed by freeze-drying a composition including chitosan. Particles 16 are embedded within the matrix. As further illustrated in FIG. 8, the particles 16 are directly surrounded by, and in contact with, the matrix. The particles 16 contain the therapeutic agent and have a coating around the therapeutic agent, the coating including chitosan so as to provide controlled release of the therapeutic agent from the particles. A quantity of the therapeutic agent may be embedded directly in the matrix as freeform agent, and not otherwise coated with chitosan. In representative examples, the freeform quantity of the therapeutic agent constitutes between 20-80% of a total quantity of the therapeutic agent in the device. Backing layer 14 is impermeable to, or at least substantially impermeable to, the passage of one or more payload components such as the particles, therapeutic agent, or additives present in the patch. Examples of backing layer materials include a non-woven polyester fabric with or without a polyacrylate adhesive and/or a clear acrylic film.

Representative examples of matrix materials and particles that may form layer 12 are provided in U.S. Patent Appl. Publ. No. 2017/0239189, where chitosan particles embedded in a chitosan-based matrix are disclosed. This prior application is hereby incorporated herein by reference in its entirety; however, the definitions provided above in paragraph 25 shall prevail over any contrary definitions in the prior application. Chitosan is a deacetylated derivative of chitin, the second most abundant polysaccharide, and has a large density of reactive groups and a wide range of molecular weights. Chitosan is considered useful as a bioadhesive material because of its ability to form non-covalent bonds with biological tissues, mainly epithelia and mucous membranes. Bioadhesions formed using natural polymers have unique properties as a carrier because they can prolong residence time and, therefore, increase the absorbance of loaded drugs. Chitosan is a bioabsorbable, biocompatible, biodegradable, anti-bacterial and non-toxic polymer.

Published application US 2017/0239189 A1 also states, in paragraph [0095], as follows: "It has been found that better results are provided if the particles are made from pure chitosan, a material characterized by not being a salt, that is, with its amine groups unprotonated, and having a degree of deacetylation of at least 70%. In particular, the particles are characterized by larger diameters than traditional particles. In some embodiments, the average diameter of the pure chitosan particles may range from about 200 to about 2000 nanometers. In other embodiments, the average diameter ranges from about 500 to about 2000 nanometers, and in additional embodiments from 500 to 1000 nm."

In addition, chitosan has different functional groups that can be modified. Because of its unique physicochemical properties, chitosan has great potential in a range of biomedical applications. Chitosan can be used as a delivery mechanism because of its bio-adhesiveness as well as its established ability to act as an absorption and permeation enhancer. The barrier in mucosa or epithelium can easily be disrupted by chitosan particles, enhancing permeability through mucosa. Chitosan has been found to be an ideal material for enabling efficacy and functionality of the patch. In the course of experiments, following surgical resection of tumors, a chitosan-based patch was applied within the surgical cavity. Only treatment with the chitosan-based patch resulted in essentially no recurrence or metastasis of cancer cells. Other patches, such as patches made of purely HPMC, pectin, alginate did not yield these same effects for unknown reasons. Chitosan is a blood coagulant, likely due to chitosan's positive charge attracting and retaining negatively-charged red blood cells upon exposure to blood, which results in coagulation [15, 16]. This coagulation, in combination with other unknown factors, may prevent the spread of free cancer cells within the bloodstream and body. In addition, chitosan loosens the tight cell junctions within tissue to increase permeation and passage of agents within tissue. This effect may, in part, prevent the spread of cancerous cells within local and systemic tissue due to cancerous cells becoming attracted towards the patch because of the cells' more acidic properties or other unknown factors. In permeation studies conducted with a number of patch materials, similar permeation of particles was noted in chitosan-based patches as well as non-chitosan-based patches, so additional permeation, in and of itself, does not result in this higher efficacy.

The most widely developed particle manufacturing methods are ionotropic gelation and self-assembling polyelectrolytes. These methods offer many advantages, such as a simple and mild preparation method without the use of organic solvent or high shear force. These methods are applicable to broad categories of agents including macromolecules which are notorious as labile agents. Usually, the factors found that affects particle formation, including particle size and surface charge, are molecular weight and degree of deacetylation of chitosan. The particles may be tailored to be stable in a variety of environments.

The ionotropic gelation method is commonly used to prepare chitosan particles. This method is based on electrostatic interaction; at physiologic pH, the primary amine groups of chitosan are protonated, and therefore chitosan is positive-charged. The positive charge is used to form particles in solution via cross-linking with polyanions (stabilizer) such as sodium tripolyphosphate (STPP), to efficiently encapsulate the drug via electrostatic interaction, and to promote cellular internalization of drug-containing chitosan particles. Polyanionic stabilizers may function as cross-linkers to form the particles by acting as a negative counter-ion to the positively charged amine groups on chitosan. This electrostatic interaction forms ionic bonds that support the structure of the particles. Also, the presence of sodium as positive counter-ion may render STPP a more effective cross-linker than other tripolyphosphate (TPP) salts.

Several advantages of this simple and mild method include the use of aqueous solutions, the preparation of particles with a small size, the manipulation of particle size by the variation in pH values, and the possibility of encapsulation of drug during particle formation. Structural changes can be introduced by ionic strength variations, like presence of KCl at low and moderate concentrations emphasize swelling and weakness of chitosan-STPP ionic interactions.

The particles can permeate tissue to deliver encapsulated agents. The particle size is dependent on the pH of the aqueous solution from which they are prepared and the weight ratio of chitosan to STPP, and the size of the particles influences the drug release rates. Other parameters affect the particles including the chitosan:stabilizer (such as STPP) ratio in aqueous solution during the synthesis process, as an increase in the amount of stabilizer leads to a higher degree of chitosan cross-linking and a decrease in the particle dimensions. Accordingly, the size of the particles can be modulated, allowing the use of specific particle size ranges tailored to the tissue for which the particles are chosen.

Once the patch is prepared, the patch is subjected to a sterilization process that ensures that the final product meets the sterility requirements of surgery applications while not appreciably degrading the components or performance of the patch. In particular, care should be taken that the sterilizing process does not significantly affect the structure and efficacy of the therapeutic agent contained in the patch. Gamma ray irradiation, which uses radiation emitted from radioactive isotopes such as Cobalt 60 to kill microorganisms, has been found to effectively sterilize patches while leaving chemotherapeutic agents essentially unaffected.

The permeability of the particles and the agent is one of the important factors to the efficacy of the patch. This attribute is designed and optimized for intra-operation chemotherapy. The agent and particles should permeate deep enough to effectively destroy the micrometastatic cells in the tissue surrounding the resected tumor, but not so deep as to be removed by the bloodstream. An example is shown in FIGS. 5A-5C, where freshly harvested porcine tissue was used to gauge permeation ability. A pig was sacrificed and patches were applied to its excised stomach tissue within a very short time. Patches contained the green fluorescent dye Fluorescein isothiocyanate (FITC) encapsulated within the particles with an average size of approximately 450 nm. Patches were synthesized according to a freeze drying method and particles were synthesized using the ionic gelation technique. The chitosan particles themselves were conjugated to the red fluorescent dye cyanine 5 (Cy5). Patches containing these two dyes were tested and the images in FIGS. 5A-5C show the results following treatment with these patches. All tissue surfaces were washed following treatment to remove any remaining fluorescence on the tissue surface. FIG. 5A is a 4× zoom overlay where the scale bar has a length of 1000 μm. The microscope used was a Life Technologies EVOS model where fluorescence was UV induced. As shown, the particles permeated into the tissue and the encapsulated agent permeated deep into tissue. FIG. 5B is a 10× zoom picture of the porcine stomach tissue. The scale bar is 400 μm long and the fluorescence patterns reveal deep permeation into the tissue. While difficult to see, the red Cy5 dye has permeated all the way to the upper right of the image. FIG. 5C is a 40× zoom of the stomach tissue. The scale bar is 100 μm. This closer image better visualizes the particles within the tissue. As shown, the red Cy5 particles can be observed scattered within the tissue.

Figure 6:
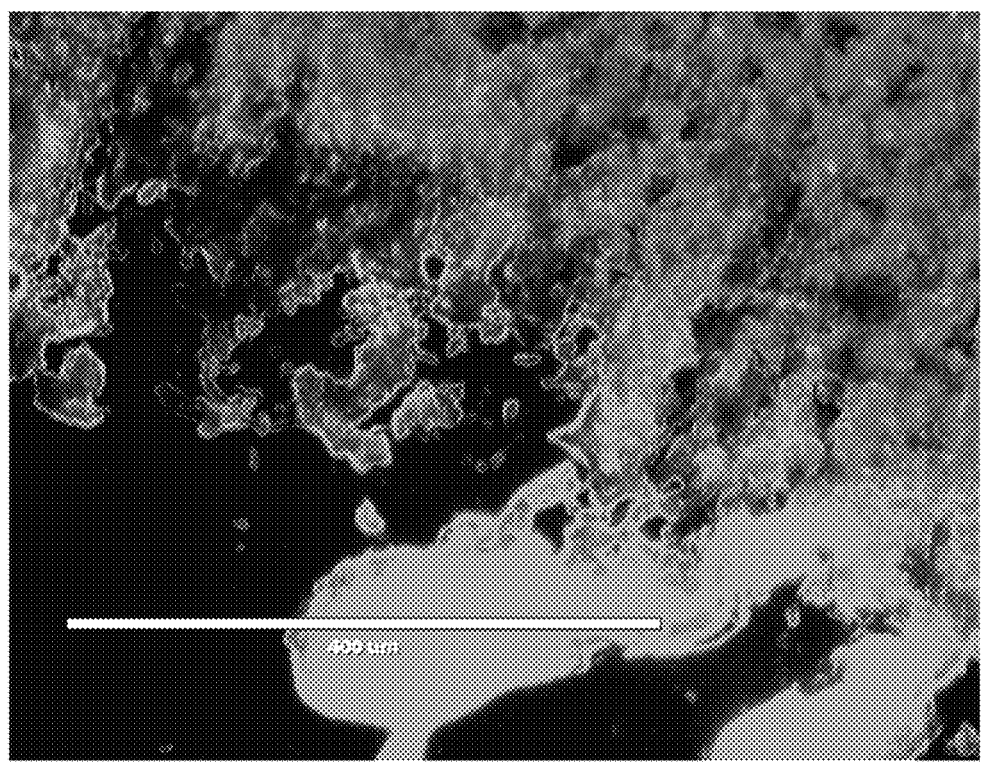
FIG. 6 is a photomicrograph showing the results from an ex vivo experiment conducted on porcine stomach tissue.

FIG. 6 shows the results of a similar experiment conducted on porcine small intestine. The image (scale bar 400 μm) shows deep permeation within the small intestine tissue of the (red/orange) particles and encapsulated agent (green). The tissue surface was washed following treatment to remove any remaining fluorescence on the tissue surface.

Figure 7:
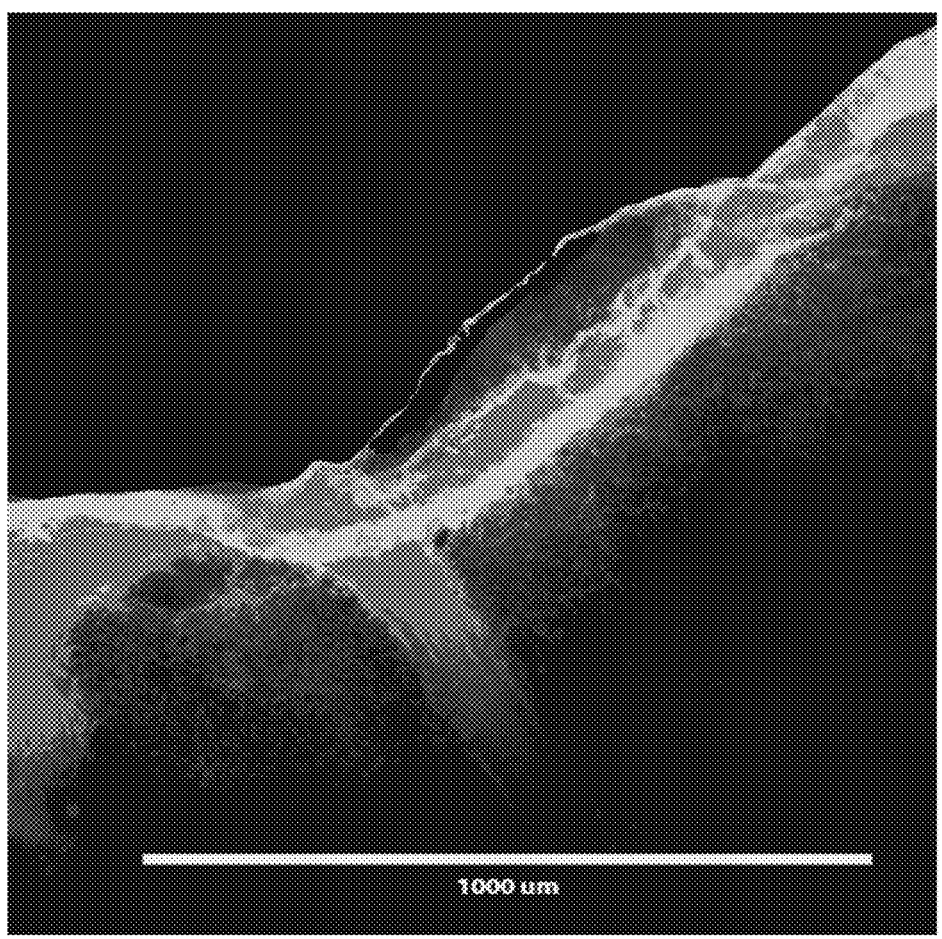
FIG. 7 is a photomicrograph showing the results from an ex vivo experiment conducted on porcine stomach tissue.

FIG. 7 shows another example of the patch with particles of different sizes included that resulted in permeation to different tissue depths. A similar experiment was conducted on porcine spleen tissue with particles having an average diameter of 600 nm. The image shows permeation of the agent labeled with FITC within the tissue of the spleen. The tissue surface was washed following treatment to remove any remaining fluorescence on the tissue surface.

In some embodiments, the patch also contains an additive including at least one of the following: (1) a particle aggregation inhibitor, (2) a particle adhesion inhibitor, and/or (3) an agent to promote hydration of the patch to facilitate particle/agent release. Example aggregation inhibitors, adhesion inhibitors, and aggregation promoters are also disclosed in the above-cited U.S. Patent Appl. Publ. No. 2017/0239189. The particles were found to inherently release poorly from the patch. In order to release the particles at a satisfactory rate and amount, at least one of these additives should be included within the composition of the patch.

The addition of a hydration promoter (propylene glycol) was experimentally tested, and was found to significantly increase release and permeation of the payload within the patch. Without wishing to be bound by any particular theory, the hydration promoter may increase moisture absorption by the delivery device, enabling the rapid release and permeation of the particles from the patch. The hydration promoter may also improve uniformity and durability by acting as a cryoprotectant during the manufacturing process of the delivery device. Again without being bound to any particular theory, the hydration promoter may act as a "spacer" between ice crystals and patch polymer molecules, to ensure a uniform freezing pattern. The resulting structure is more flexible, uniform, and durable than in the absence of the hydration promoter.

Figure 10:
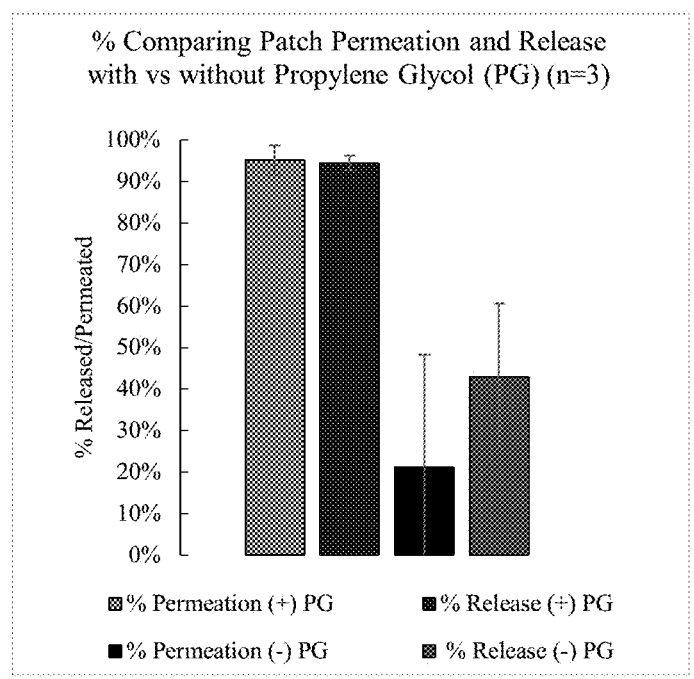

To illustrate the improvement in performance imparted by hydration promoters, patches including a chitosan polymer and chitosan particles were manufactured with and without propylene glycol (PG) in the patch body. The particle release and permeation of the patches was measured for both types of patch, and the experiment was run in triplicate. As reported in the chart of FIG. 10, the average percentage of permeation in the presence of propylene glycol ((+)PG) was 94% with a standard deviation of about 3%, which dropped to 43% with a standard deviation of 27% in the absence of propylene glycol ((−)PG). The percentage of release in the presence of propylene glycol was 95% with a standard deviation of about 3%, as opposed to 21% with a standard deviation of 41% without PG. Clearly, patches with PG performed markedly better than those without, and release and permeation numbers were more reproducible as shown by the smaller standard deviations.

In some embodiments, there are provided patches whose functionality is improved by the addition of an adhesion inhibitor. Without wishing to be bound to any particular theory, when the patch and particles are made of materials bearing polar or ionically charged moieties, such as chitosan, the mobility of the particles suffers. In the instance of chitosan, the interactions between acetyl and amine moieties of the polymer may cause the particles to adhere to the patch body and inhibit their release. The inclusion of an adhesion inhibitor may mitigate adhesion of the patch with the particles. Again without being bound to any particular theory, the adhesion inhibitor may act as a "spacer" between the chitosan of the particles and the chitosan in the body of the patch, releasing the particles and allowing for improved drug release profiles.

Representative example adhesion inhibitors include non-ionic polymers such as hydroxypropyl methylcellulose (HPMC). Depending on the application, the molar mass of the non-ionic polymer may be from about 1 kDa to about 200,000 kDa, while its viscosity may vary from about 10 cps to 100,000 cps. In representative embodiments, the molar mass of the non-ionic polymer is from about 10 kDa to 30 kDa, and its viscosity from about 10 cps to about 100 cps. Depending on the application, the amount of adhesion inhibitor may be from about 0.1 wt % to about 99 wt % of total patch weight. In some embodiments, the amount of adhesion inhibitor is from about 0.1 wt % to about 25 wt %.

In some embodiments, the functionality of the patch is improved by the addition of an aggregation inhibitor. Processes for manufacturing the delivery devices include freezing steps during which ice crystals may form within the patch. Such crystals can force the particles into each other, creating particle aggregates where the particles are damaged or destroyed. Without wishing to be bound to any particular theory, aggregation inhibitors may exert a cryoprotectant action by forming crystal microstructures which prevent aggregation of the particles. Sugars and sugar derivatives provide exemplary types of aggregation inhibitors, including monosaccharides, disaccharides, sugar alcohols, chlorinated monosaccharides, and chlorinated disaccharides such as sucralose. Depending on the application, the amount of aggregation inhibitor in the patch may be in the range from about 0.1 to about 50 wt %. In some embodiments, the amount of aggregation inhibitor is from about 1 to about 10 wt %.

Figure 9A:
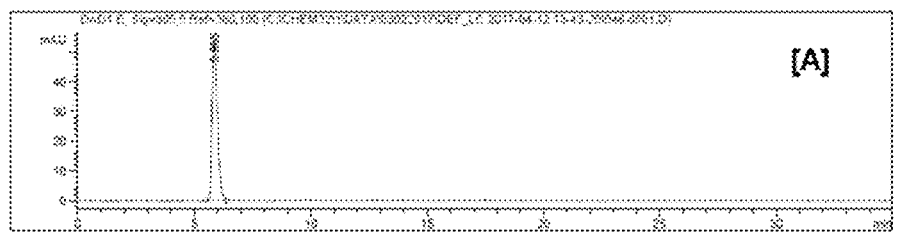
FIGS. 9A, 9B, and 9C are graphs showing that agent(s) included within a patch, according to embodiments of the present invention, are not modified when incorporated into the patch or when the patch is sterilized.
Figure 9B:
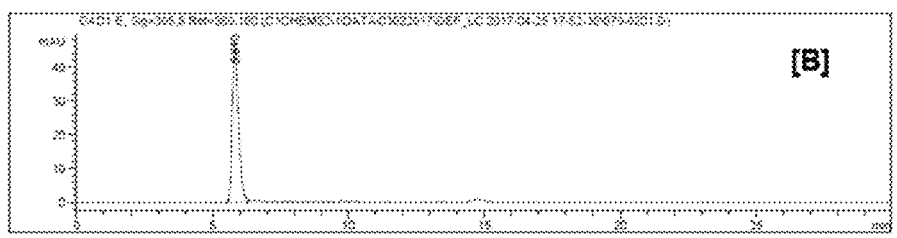
Figure 9C:
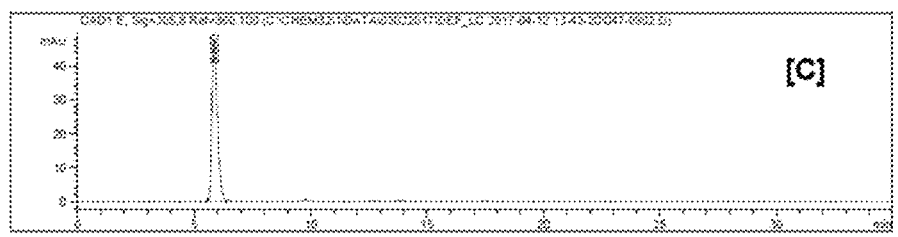

The patch is sterilized prior to application to a surgical cavity, for example after the patch is manufactured and before packaging. In some embodiments, gamma sterilization is employed to sterilize the patch. FIGS. 9A-9C show HPLC chromatograms at various stages of product synthesis. The HPLC apparatus was an Agilent 1100 Series HPLC using a water/methanol/sodium lauryl sulfate solvent mixture adjusted to pH 2.5 with trifluoromethanesulfonic acid. FIG. 9A is an HPLC chromatogram of a cisplatin standard. FIG. 9B is an HPLC chromatogram of a cisplatin sample taken from a patch that was dissolved in a solution, which illustrates that the cisplatin was not modified while in the patch. FIG. 9C is an HPLC chromatogram of cisplatin extracted from a patch which underwent gamma ray sterilization for 25 minutes, and further shows that cisplatin was not modified. Similar experiments were conducted using oxaliplatin and 5-fluorouracil. This experiment proves that the patches are able to be manufactured and sterilized while maintaining the integrity of the agent(s) included within.

Figure 8:
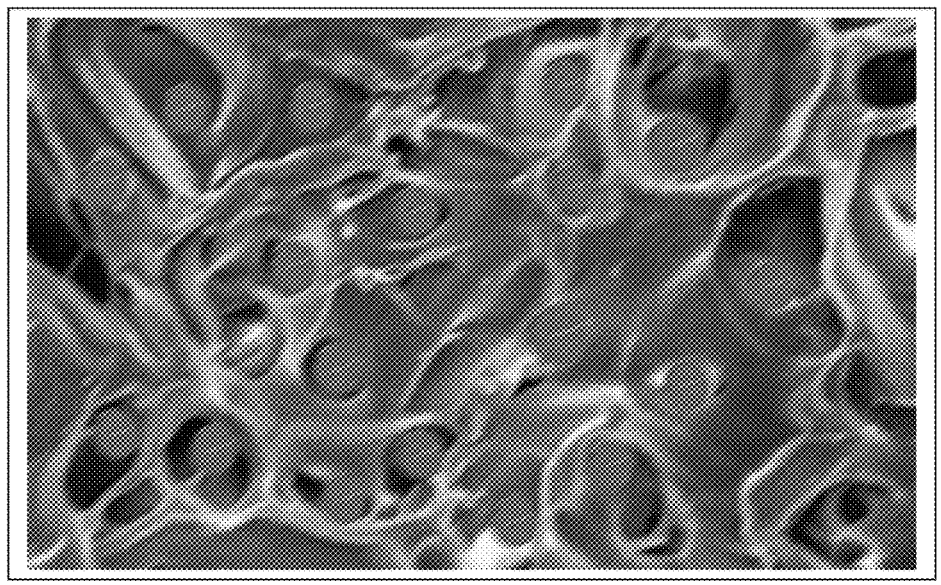
FIG. 8 is an image of the matrix of an example patch overlaid with a brightened depiction of particles embedded within the matrix which are released upon application of the patch to tissue according to embodiments of the present invention.

In some embodiments, the patch is formed with one side exposed for contact with the appropriate tissue. Particles containing the agent or agents will be released from this side upon contact with the appropriate tissue. As illustrated in FIG. 8 the particles (round) are held within the body of the patch. The body of the patch is the web-like material, which is primarily comprised of chitosan. In some embodiments, the other side facing the external cavity may be adjacent to a backing layer 14, for instance a film, coating, or impermeable membrane to prevent significant loss of one or more payload components from the patch into the tissue/cavity on the opposite side from the desired tissue. This backing layer 14 may also prevent contamination of the patch with fluids or other matter that may be present.

The patch makes use of well-known chemotherapeutics in some embodiments as well as commercially available excipients, additionally minimizing the costs associated with its manufacture. The simple manufacturing process, relatively low overall costs, and easy method of administration serve as improvements over all existing intraoperative treatment methods, and will promote a widespread uptake and utilization of the present invention.

In some embodiments, the patch contains a combination of two or more chemotherapeutics to be delivered to a surgical cavity within the abdomen, pelvis and/or intraperitoneal region, where each of the chemotherapeutics is present at some ratio of freeform chemotherapeutic to particle-encapsulated chemotherapeutic. In some embodiments where two or more chemotherapeutics are included, one chemotherapeutic may be encapsulated within particles while the other remains freeform. For example, if cisplatin and oxaliplatin are desired chemotherapeutics for inclusion within the patch, one such chemotherapeutic (cisplatin) may be included in particle form while oxaliplatin may be included in freeform.

In other embodiments where two or more chemotherapeutics are included, one chemotherapeutic may be encapsulated within particles while the other exists both in freeform and within particles. For example, if cisplatin and oxaliplatin are desired chemotherapeutics for inclusion within the patch, one such chemotherapeutic (cisplatin) may be included in particle form while oxaliplatin may be included both in freeform and encapsulated within particles. In additional embodiments where two or more chemotherapeutics are included, two or more of the chemotherapeutics may be included both within particles and both in freeform. For example, if cisplatin and oxaliplatin are desired chemotherapeutics for inclusion within the patch, both cisplatin and oxaliplatin may exist encapsulated both within particles and additionally in freeform at a desired ratio within the final patch product.

In some embodiments, at least one agent included within the patch is an anti-infective agent, which may be included in freeform, encapsulated within particles, or a combination thereof. In some embodiments, at least one agent included within the patch is an anti-bacterial or anti-viral agent, which may be included in freeform, encapsulated within particles, or a combination thereof. In some embodiments, the majority of particles range in diameter from 60 nanometers to 2 microns. In a set of preferred embodiments, the particles have an average diameter between 100 nm and 1000 nm. More preferably, the particles have an average diameter of 200-500 nm or of 100 to 400 nm.

In some embodiments, at least one patch is included as a component of a kit for the treatment of abdominal, pelvic and/or intraperitoneal diseases which are accessible via surgery. This kit may include materials that are required for proper administration of the patch as well as proper and safe disposal of the patch after application and cleaning of the treated area. For example, FOLFOX (5-FU, leucovorin, and oxaliplatin) or CapeOx (capecitabine and oxaliplatin) regimens are known, common agents for the treatment of traditional colon cancer. These chemotherapeutics can be utilized in a safe manner to topically treat colon tumors which may have metastasized within the abdomen/pelvis. However, extensive precautions must be taken to ensure that (1) proper handling procedures are followed during treatment, (2) time to prepare and administer the patch is reduced to minimize the time within which the patient's abdomen/pelvis remain exposed, and (3) ensure that contact is minimized between these agents and both the patient and personnel applying the patch. Items that may then be included in the kit for the purpose of safety can include forceps or other tools for the placement of the patch, disposable packaging for any remaining portion of the patch after application and other safety components.

In addition, a permeation enhancing agent may be included within the kit. The permeation enhancer may be applied briefly prior to application of the patch. Example classes of permeation enhancing agents include bile salts, fatty acids, glycerides, polyacrylic acid derivatives, chelating agents, nitric oxide donors, salicylates, chitosan, and zona occludens toxins, and specific example permeation enhancers include dodecyl-2 (N,N-dimethylamino) propionate, sodium cholate sodium deoxycholate, sodium glycodeoxycholate, sodium taurocholate, sodium glycocholate, and N-lauryl-b-maltopyranoside. Certain surfactants may serve as permeation enhancing agents, for instance Poloxymer 407, Poloxymer 188, Tween 20, Span 20, oleic acid, sodium dodecyl sulfate, sodium lauryl sulfate, Polysorbate 80, and lauryl esters.

The embodiments of the described above are intended to be merely exemplary; numerous variations and modifications will be apparent to those skilled in the art. All such variations and modifications are intended to be within the scope of the present invention as defined in the appended claims.

REFERENCES

[1] "What Is Metastatic Cancer?" *American Cancer Society*. N.p., n.d. Web. 25 Apr. 2017.
[2] "Metastatic Cancer." *National Cancer Institute*. N.p., n.d. Web. 25 Apr. 2017.

[3] Hanna Dillekås, Monica Transeth, Martin Pilskog et al. "Differences in metastatic patterns in relation to time between primary surgery and first relapse from breast cancer suggest synchronized growth of dormant micrometastases". Breast Cancer Res Treat. 2014; 146(3): 627-636.
[4] Tufts Medical Center "Cytoreductive Surgery with Hyperthermic Intraperitoneal Chemotherapy (HIPEC)."
[5] Zhang W, Zhong D, Liu Q et al. "Effect of chitosan and carboxymethyl chitosan on fibrinogen structure and blood coagulation." J Biomater Sci Polym Ed. 2013; 24(13): 1549-63. doi: 10.1080/09205063.2013.777229.
[6] Elena Sperk, Daniela Astor, Anke Keller et al. "A cohort analysis to identify eligible patients for intraoperative radiotherapy (TORT) of early breast cancer" Radiation Oncology 20149:154 DOI: 10.1186/1748-717X-9-154.
[7] Tulunay et al, Pilot study of intraoperative chemotherapy with cisplatin and 5-Fluorouracil in patients with advances squamous cell carcinoma of the head and neck- 2006 in Wiley InterScience, DOI: 10.1002/hed. 20521.
[8] Harless et al, Revisiting perioperative chemotherapy: the critical importance of targeting residual cancer prior to wound healing, Published: 22 Apr. 2009, BMC Cancer 2009, 9:118 doi: 10.1186/1471-2407-9-118.
[9] West Virginia University. "ORT Intraoperative Radiation Therapy" medicine Health Report.
[10] Cancer Treatment Centers of America. "IORT Medical Animation". CTCA Cancer Videos." CancerCenter.com
[11] New Radiant Technology S.p.A. "Novac 7, The First mobile electron linear accelerator for IORT" http://sen-newald.de/wp-content/uploads/novac7.pdf
[12] Tufts Medical Center "Cytoreductive Surgery with Hyperthermic Intraperitoneal Chemotherapy (HIPEC)"
[13] Cancer Treatment Centers of America. "Hyperthermic intraperitoneal chemotherapy (HIPEC)". CancerCenter.com
[14] Northwestern University. "When Fighting Cancer Isn't Worth It", Mary Mulcahy, Jan. 4 2013.
[15] Tianhong Dai et al, Chitosan preparations for wounds and burns: antimicrobial and wound-healing effects, Expert Rev Anti Infect Therapy. 2011 July; 9(7): 857-879.
[16] Biodegradability of Chitin and Chitosan Containing Films in Soil Environment; Journal of Environmental Polymer Degradation Vol. 3 No. 1 1995. Makarios-Laham, Tung-Ching Lee.

What is claimed is:

1. A device for rapid delivery of a therapeutic agent to a surgical cavity, the device comprising:
   a porous, mucoadhesive, freeze-dried polymeric matrix having first and second opposed surfaces, the matrix formed by a composition comprising chitosan, and a particle adhesion inhibitor, comprising hydroxypropylmethylcellulose (HPMC);
   a plurality of particles, having an average diameter between 500 nm and 2000 nm, embedded within the matrix so as to be directly surrounded by, and in contact with, the matrix, the particles containing the therapeutic agent and having a coating around the therapeutic agent, the coating comprising chitosan so as to provide controlled release of the therapeutic agent from the particles through the first opposed surface of the matrix; and
   one or more additives selected from the group consisting of a hydration promoter, a particle aggregation inhibitor, and combinations thereof,
   wherein:
   the first surface of the matrix is configured to be applied to the surgical cavity;
   the device is configured to provide release of the particles through the first surface;
   the device is sterilized;
   the device provides release of approximately 20% to 100% of the therapeutic agent within 20 minutes of application to the surgical cavity, and
   the particle adhesion inhibitor, and, when present, the hydration promoter, and the particle aggregation inhibitor are compounds mutually distinct from one another and present in amounts sufficient to achieve the controlled release of the particles without preventing formation of the freeze-dried matrix.

2. A device according to claim 1, wherein the hydration promoter is selected from the group consisting of ethylene glycol, propylene glycol, beta-propylene glycol, glycerol and combinations thereof.

3. A device according to claim 1, wherein the particle aggregation inhibitor is selected from the group consisting of monosaccharides, disaccharides, sugar alcohols, chlorinated monosaccharides, chlorinated disaccharides, and combinations thereof.

4. A device according to claim 1, wherein the particles further include sodium tripolyphosphate.

5. A device according to claim 1, further comprising a free quantity of the therapeutic agent, embedded directly in the matrix, and not otherwise coated with chitosan, wherein the free quantity of the therapeutic agent constitutes between 20-80% of a total quantity of therapeutic agent in the device.

6. A device according to claim 1, further comprising a backing layer disposed on the second surface, wherein the backing layer prevents significant loss of payload components in the device from diffusion through the second surface, and optionally protects the device from an environment.

7. A device according to claim 6, wherein the backing layer includes a material selected from the group consisting of a polyacrylate adhesive, a non-woven polyester fabric backing, and combinations thereof.

8. A device according to claim 1, wherein the therapeutic agent is a chemotherapeutic pharmaceutical.

9. A device according to claim 8, wherein the chemotherapeutic is selected from the group consisting of platinum-based chemotherapeutics, 5-flurouracil, and combinations thereof.

10. A device according to claim 1, wherein the therapeutic agent is an agent selected from the group consisting of anti-infective, anti-bacterial, or anti-viral agent, and combinations thereof.

11. A kit comprising the device according to claim 1 and a permeation enhancing agent selected from the group consisting of dodecyl-2-(N,N-dimethylamino) propionate, bile salts, surfactants, fatty acids, glycerides, polyacrylic acid derivatives, chelating agents, nitric oxide donors, salicylates, chitosan, zona occludens toxins, and combinations thereof.

12. A kit according to claim 11, wherein the permeation enhancing agent is selected from the group consisting of sodium cholate, sodium deoxycholate, sodium glycodeoxycholate, sodium taurocholate, sodium glycocholate, N-lauryl-b-maltopyranoside, and combinations thereof.

13. A kit according to claim 11, wherein the surfactant is selected from the group consisting of oleic acid, sodium dodecyl sulfate, sodium lauryl sulfate, polysorbate 80, lauryl esters, and combinations thereof.

14. A method for manufacturing a device according to claim 1, the method comprising:

forming a first mixture with a plurality of particles having an average diameter between 500 nm and 2000 nm, the particles containing a therapeutic agent and having a coating around the therapeutic agent, the coating including chitosan;

adding chitosan a particle adhesion inhibitor comprising HPMC, and one or more additives selected from a group consisting of a hydration promoter, a particle aggregation inhibitor and combinations thereof to the first mixture, to form a second mixture;

freezing the second mixture in a bath containing an aqueous alcoholic solution at a temperature above the freezing temperature of the aqueous alcoholic solution and at most −40° C., to form a frozen layer precursor;

drying the frozen layer precursor, to form a porous patch with particles embedded within a polymeric matrix of the patch; and sterilizing the patch.

15. A method according to claim 14, wherein the bath further contains dry ice.

16. A method according to claim 14, wherein the alcohol of the aqueous alcoholic solution is ethanol.

17. A method according to claim 14, wherein the aqueous alcoholic solution is from about 90 wt % ethanol to about 99 wt % ethanol.

18. A method according to claim 14, wherein a free quantity of the therapeutic agent is embedded directly in the matrix, and not otherwise coated with chitosan, wherein the free quantity of the therapeutic agent constitutes between 20-80% of a total quantity of therapeutic agent in the device.

19. A method according to claim 14, wherein the patch includes first and second opposed surfaces and the first surface is configured to be applied to the tissue, the method further comprising adhering a backing layer to the second surface of the patch, wherein the backing layer prevents significant loss of payload components in the patch from diffusion through the second surface, and optionally protects the patch from an environment.

20. A method according to claim 14, wherein the drying is under vacuum.

21. A method according to claim 14, wherein the sterilizing includes gamma ray irradiation.

* * * * *